US006552194B2

(12) United States Patent
Lang et al.

(10) Patent No.: US 6,552,194 B2
(45) Date of Patent: *Apr. 22, 2003

(54) PROCESS FOR THE PREPARATION OF PURE TRIETHYLENEDIAMINE (TEDA)

(75) Inventors: Ortmund Lang, Quirnbach (DE); Bernd Rumpf, Hockenheim (DE); Matthias Frauenkron, Ludwigshafen (DE); Dirk Funhoff, Mannheim (DE); Thomas Manderbach, Ludwigshafen (DE); Bernd Stein, Seeheim-Jugenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/033,915

(22) Filed: Jan. 3, 2002

(65) Prior Publication Data

US 2002/0156278 A1 Oct. 24, 2002

(30) Foreign Application Priority Data

Jan. 10, 2001 (DE) .......................... 101 00 943

(51) Int. Cl.$^7$ ............................................ C07D 487/08
(52) U.S. Cl. ....................................... 544/352
(58) Field of Search .......................... 544/352

(56) References Cited

U.S. PATENT DOCUMENTS

| 902,073 A | 10/1908 | Guerity |
| 2,937,176 A | 5/1960 | Herrick ........................ 260/268 |
| 3,123,607 A | 3/1964 | Farkas |
| 3,297,701 A | 1/1967 | Brader |
| 3,993,651 A | 11/1976 | Keating |
| 4,017,494 A | 4/1977 | Bosche |
| 4,182,864 A | 1/1980 | Nieh et al. ................... 544/352 |
| 4,216,323 A | 8/1980 | Otsuki |
| 4,233,447 A | 11/1980 | Nieh et al. ................... 544/352 |
| 4,289,881 A | 9/1981 | Imre et al. ................... 544/352 |
| 4,757,143 A | 7/1988 | Vanderpool |
| 4,804,758 A | 2/1989 | Hoelderich |
| 5,741,906 A | 4/1998 | Santiesteban |

FOREIGN PATENT DOCUMENTS

| DE | 1 745 627 | 5/1970 |
| DE | 24 42 929 | 3/1976 |
| DE | 26 11 069 | 9/1976 |
| DE | 28 49 993 | 5/1979 |
| DE | 37 18 395 | 12/1987 |
| DE | 36 34 258 | 4/1988 |
| EP | 111 928 | 6/1984 |
| EP | 382 055 | 8/1990 |
| EP | 842 935 | 5/1998 |
| EP | 1 070 717 | 1/2001 |
| GB | 902073 | 7/1962 |
| GB | 2 080 283 | 2/1982 |
| JP | 49-048609 | 5/1974 |

OTHER PUBLICATIONS

Derwent Abstract for JP 62240674 (1988).*
JP 49–048609 Translation.

* cited by examiner

Primary Examiner—Mark L. Berch
(74) Attorney, Agent, or Firm—Keil & Weinkauf

(57) ABSTRACT

The invention relates to the preparation of pure triethylenediamine (TEDA) by evaporating TEDA from the mixture comprising a solvent or diluent, where the solvent or diluent has a boiling point at atmospheric pressure in the range from 175 to 250° C., passing the vapor-form TEDA into a liquid solvent, and subsequently crystallizing the TEDA out of the resultant solution.

13 Claims, No Drawings

PROCESS FOR THE PREPARATION OF PURE TRIETHYLENEDIAMINE (TEDA)

The present invention relates to a process for the preparation of pure triethylenediamine (=TEDA=DABCO®=1,4-diazabicyclo[2.2.2]octane) and solutions thereof.

Triethylendiamine (TEDA), which is a solid under normal conditions, is an important catalyst for the production of polyurethane foams.

For this and other areas of application, a pure TEDA with the lowest possible odor and a pure-white color with the least possible discoloration, for example with the lowest possible APHA color number (DINISO 6271) which retains these properties even over extended storage times (of, for example, 6, 12 or more months) is desired.

Various processes are known for the preparation and purification of TEDA:

DT-A-24 42 929 relates to a process for the preparation of TEDA by elimination of glycol from N,N'-di(hydroxyethyl)piperazine in the presence of $Al_2O_3$ as catalyst.

U.S. Pat. No. 3,297,701 discloses a process for the preparation of diazabicyclo[2.2.2]octanes by reaction of corresponding hydroxyethyl- or aminoethylpiperazines at elevated temperature in the presence of metal phosphates, for example calcium phosphate.

DE-A-36 34 258 describes a process for the preparation of diazabicyclo[2.2.2]octanes by reaction of corresponding hydroxyethyl- or aminoethylpiperazines in the presence of zirconium phosphates.

DE-A-1 745 627 relates to a process for the preparation of TEDA and piperazine by reaction of an ethylenediamine on an acidic silica/alumina catalyst at elevated temperature and isolation of the TEDA by distillation and/or crystallization.

DE-A-37 18 395 describes the preparation of TEDA by reaction of an acyclic hydroxyethylethylenepolyamine and/or cyclic hydroxyethylethylenepolyamine in the presence of a phosphorus-containing titanium dioxide or zirconium dioxide catalyst.

EP-A-111 928 describes the use of certain phosphate catalysts, for example mono- or pyrophosphates of magnesium, calcium, barium or aluminum, in organic condensation reactions, for example the conversion of N-(2-hydroxyethyl)piperazine into TEDA.

EP-A-382 055 discloses a process for the preparation of TEDA in which 1,2-diaminoethane and from 0 to 200 mol % of piperazine are reacted at elevated temperature on Al, B, Ga and/or Fe silicate zeolites.

EP-A-842 935 describes a process for the preparation of TEDA by conversion of an amine compound, such as monoethanolamine, into a product comprising TEDA and piperazine on a catalyst, followed by reaction of this product with an ethylating compound containing at least one N and/or O atom in the presence of a shape-selective zeolite catalyst.

U.S. Pat. No. 5,741,906 relates to the preparation of TEDA by reaction of an amine compound, such as monoethanolamine, on a zeolite catalyst of the pentasil type.

The known processes for the preparation of TEDA result in the formation of crude reaction products which, besides TEDA, also contain water, by-products, for example piperazine and high-molecular-weight polymers, and any solvent employed in the reaction. TEDA is usually separated off from these mixtures by batch or continuous distillation or rectification and is usually purified in a subsequent step by crystallization or recrystallization.

Owing to its properties [hygroscopic, heat-sensitive, boiling point (174° C. at atmospheric pressure) and melting point (158–160° C.) close to one another], TEDA can be handled with difficulty and only with corresponding technical effort without an impairment in the quality of the TEDA with respect to color, color stability (undesired increase in the color number, for example measured as the APHA color number, over the storage time), odor (undesired smell of cyclic saturated N-heterocyclic compounds having 5-membered rings or other cyclic saturated N-heterocyclic compounds having 6-membered rings and/or aromatic N-heterocyclic compounds having 5- or 6-membered rings) and purity taking place.

The TEDA obtained by the known processes after distillation or rectification and solutions prepared therefrom is/are usually unmarketable owing to the color (for example measured as APHA color number), color stability and/or odor, and only through one or more further purification step(s), such as technically complex crystallization or recrystallization, in some cases in a number of steps, is it possible to improve the TEDA quality.

There has therefore been no lack of attempts to find alternative processes for the preparation of TEDA in improved quality.

DT-A-26 11 069 relates to the isolation of TEDA in which propylene glycol is added to the crude TEDA, and the mixture is subsequently subjected to fractional distillation.

DE-A-28 49 993 discloses a process for the separation and isolation of TEDA in which water is added to the crude TEDA, and the mixture is subsequently distilled.

JP-A-49 048 609 claims a process for the purification of piperazine and/or TEDA by fractional distillation of a mixture comprising piperazine and/or TEDA, comprising the steps of dissolution of the piperazine and/or TEDA distillates in water or an organic solvent, it being possible for the solvent to be in liquid or gas form, and collection of the solutions of the distillates. According to the application, this process achieves the object of preventing blockages by solids in the distillation apparatus. The description, the diagrammatic representation of the distillation apparatus and the examples in this patent application teach that, to this end, the piperazine or the TEDA is firstly liquefied in a condenser at the top of the distillation column and only thereafter dissolved in the solvent.

This process has the disadvantage that it does not give TEDA in the desired quality.

The earlier German patent applications 19933850.7 of Jul. 23, 1999, and 19962455.0 of Dec. 22, 1999, relate to a process for the preparation of a solution of pure TEDA in which TEDA is evaporated, and the vapor-form TEDA is passed into a liquid solvent, and to a process for the preparation of pure TEDA in which TEDA is crystallized out of this solution.

It is an object of the present invention to find an improved, efficient and economical process for the preparation of pure triethylenediamine (TEDA) and solutions thereof which gives TEDA and TEDA solutions of improved quality with respect to color, color stability, odor and purity.

We have found that this object is achieved by a process for the preparation of a solution of pure triethylenediamine (TEDA) which comprises evaporating TEDA from a mixture comprising a solvent or diluent, where the solvent or diluent has a boiling point at atmospheric pressure (=1.01325 bar) in the range from 175 to 250° C., and passing the vapor-form TEDA into a liquid solvent.

Subsequent crystallization of the TEDA out of the resultant solution gives pure TEDA having the quality improved in accordance with the object.

The solvent in whose presence the TEDA is evaporated and the solvent into which the vapor-form TEDA is passed may be the same or alternatively different solvents.

The process according to the invention, in which the passing of the vapor-form TEDA into a liquid solvent is also referred to below as TEDA quenching, significantly reduces the formation of undesired by-products and decomposition products which result in a reduction in the quality of the TEDA.

The liquid physical state of the TEDA at the outlet of the evaporation apparatus, for example rectification or distillation apparatus, is avoided in accordance with the invention, with the liquefaction of the distillate that is usual in distillations not taking place. The vapor-form TEDA is instead passed directly into a liquid solvent.

The solvent or diluent present in the mixture from which the TEDA is evaporated preferably has a boiling point at atmospheric pressure in the range from 180 to 250° C., particularly in the range from 180 to 230° C., in particular in the range from 190 to 210° C.

Suitable solvents or diluents present in the mixture from which the TEDA is evaporated are, in particular, inert polar aprotic solvents [for example N-alkyl-2-pyrrolidones (such as N-methyl-2-pyrrolidone (NMP), 1-ethyl-2-pyrrolidone, 1,5-dimethyl-2-pyrrolidone or 1-isopropyl-2-pyrrolidone), ethers (such as diethylene glycol diethyl ether, triethylene glycol dimethyl ether or triethylene glycol diethyl ether), ketones (such as acetophenone or propiophenone), lactones (such as γ-butyrolactone), sulfoxides (such as dimethyl sulfoxide), carboxylic acid esters (such as dimethyl fumarate), nitriles (such as benzonitrile) and ureas (such as 1,3-dimethylimidazolidin-2-one (DMEU) or tetramethylurea)], cyclic or acyclic hydrocarbons, in particular saturated cyclic or acyclic hydrocarbons (for example undecane, dodecane, cis-decalin or trans-decalin), chlorinated aliphatic hydrocarbons (for example 1-chlorooctane or 1,1-dichlorooctane), aromatic hydrocarbons, nitroaromatic compounds and phenols (for example naphthalene, n-butylbenzene, phenol, cresol, nitrobenzene or nitrophenol), chlorinated aromatic hydrocarbons (for example 1,2-dichlorobenzene, benzyl chloride, 1,2,3,4-tetramethylbenzene or 1,2,3,5-tetramethylbenzene), alcohols (for example benzyl alcohol, 2-ethylhexanol, 1-octanol, i-decanol, 1,2-propanediol, 1,3-propanediol, ethylene glycol, diethylene glycol, 1,2-propylene glycol, 1,3-propylene glycol, 1,2-butanediol, 1,3-butanediol, 2,3-butanediol, 1,4-butanediol, neopentyl glycol, diethylene glycol monomethyl ether or dipropylene glycol), primary, secondary and tertiary amines (for example tri-n-butylamine, benzylamine, aniline, N-ethylaniline, N,N-dimethylaniline or N,N-diethylaniline), N-alkylamides (for example N-methylformamide or N-methylacetamide), and mixtures thereof.

Particular preference is given to polar aprotic solvents having an $E^N_T$ value of from 0.1 to 0.6, particularly from 0.2 to 0.5, in particular from 0.3 to 0.45.

(For the definition of the $E^N_T$ value, see Ch. Reichardt, Solvents and solvent effects in organic chemistry, 2nd Edition, VCH 1988).

Very particularly preferred solvents are NMP and ethylene glycol.

The solvent or diluent present in the mixture from which the TEDA is evaporated is preferably added to the crude or still impure TEDA after the synthesis of the TEDA. The solvent is advantageously introduced into the bottom of the column for the TEDA distillation.

The solvent or diluent can be employed in a single pass through the apparatus or, after removal of the high-boiling components, as a circulating solution. The amount of solvent or diluent used is not essential to the invention and is selected in accordance with expediency points of view. In general, the procedure followed is such that, depending on the type of solvent or diluent, solutions or mixtures having a TEDA content of from about 1 to 90% by weight, preferably from 40 to 70% by weight, are obtained.

The TEDA evaporation according to the invention from a mixture comprising a solvent or diluent can be carried out by processes and under conditions which are familiar to the person skilled in the art, for example in a distillation or rectification apparatus, with the TEDA or a mixture comprising the TEDA (crude TEDA) being introduced in each case together with the solvent or diluent.

The vapor-form TEDA is preferably obtained at the top or at a side take-off of a distillation column. The vapor-form TEDA in the process according to the invention generally has a purity of greater than 90% by weight, preferably greater than 95% by weight, in particular greater than 97% by weight.

The residence time and thus the thermal load are advantageously kept low in the distillative work-up of the TEDA by design measures on columns and/or evaporators (for example minimization of the still volume) and/or by the use of thermally gentle evaporation methods (for example falling-film evaporator or thin-film evaporator).

In general, the temperature of the mixture comprising TEDA and the solvent or diluent from which the TEDA is evaporated in accordance-with the invention (for example the still of the corresponding TEDA distillation column) is set to 230° C., preferably from 190 to 210° C., through the choice of the solvent or diluent to be employed, the TEDA content of the mixture and/or the pressure. The absolute pressure here is generally from 0.1 to 5 bar, preferably from 0.5 to 1.5 bar.

The time duration between formation of the vapor-form TEDA used in the process according to the invention and the TEDA quench is advantageously ≦10 seconds.

Particularly suitable solvents for the TEDA quench are cyclic or acyclic (=aliphatic) hydrocarbons (in particular branched or unbranched alkanes or alkane mixtures, for example n-pentane, isopentane, cyclopentane, hexane, cyclohexane, heptane, octane or petroleum ether), chlorinated aliphatic hydrocarbons (in particular chlorinated alkanes, for example dichloromethane, trichloromethane, dichloroethane or trichloroethane), aromatic hydrocarbons (for example benzene, toluene or xylenes), chlorinated aromatic hydrocarbons (for example chlorobenzene), alcohols (for example methanol, ethanol, ethylene glycol, 1,4-butanediol and polyether alcohols, in particular polyalkylene glycols, such as diethylene glycol or dipropylene glycol), ketones (in particular aliphatic ketones, such as acetone, methyl ethyl ketone or diethyl ketone), aliphatic carboxylic acid esters (for example methyl acetate or ethyl acetate), aliphatic nitriles (for example acetonitrile or propionitrile), ethers (for example dioxane, THF, diethyl ether or ethylene glycol dimethyl ether), and mixtures thereof.

For the preparation according to the invention of a solution of pure TEDA which can be used, for example, as catalyst solution in the production of polyurethane foam, the solvent used for the TEDA quench is preferably an alcohol (for example ethylene glycol, 1,4-butanediol or dipropylene glycol). The color number of a 33% strength by weight TEDA solution in dipropylene glycol obtained in this way is less than 150 APHA, in particular less than 100 APHA.

For the preparation according to the invention of pure (crystalline) TEDA, the solvent used for the TEDA quench is preferably an aliphatic hydrocarbon, in particular a saturated aliphatic hydrocarbon having from 5 to 8 carbon atoms (for example pentane, hexane or heptane). The crystallization of the pure TEDA from the TEDA solution prepared in accordance with the invention can be carried out by methods known to the person skilled in the art. The TEDA crystals obtained by subsequent multistep or preferably single-step crystallization are of high purity (purity of in general at least 99.5% by weight, in particular at least 99.9% by weight), and the color number of a 33% strength by weight solution in dipropylene glycol is less than 50 APHA, in particular less than 30 APHA.

The vapor-form TEDA is passed into the liquid solvent in a quenching apparatus, for example preferably in a falling-film condenser (thin-film, trickle-film or falling-flow condenser) or in a nozzle apparatus. The vapor-form TEDA here can be passed in co-current or in countercurrent to the liquid solvent. The vapor-form TEDA is advantageously introduced into the quenching apparatus from the top. Tangential feed of the liquid solvent at the top of the failing-film condenser or feed of the liquid solvent through one or more nozzles is furthermore advantageous for achieving complete wetting of the inside wall of the quenching apparatus.

The solvent for the TEDA quench can be employed in a single passage through the apparatus or as a circulating solution. The amount of solvent used in the TEDA quench is not essential to the invention and is selected depending on expediency points of view. In general, a procedure is followed in which, depending on the type of solvent, solutions having a TEDA content of from about 1 to 50% by weight, preferably from 20 to 40% by weight, are obtained.

In general, the temperature in the TEDA quench is set to from 20 to 100° C., preferably from 30 to 60° C., by temperature-control of the solvent employed and/or of the quench apparatus.

The absolute pressure in the TEDA quench is generally from 0.5 to 1.5 bar.

The gas space in the quench apparatus is saturated with solvent vapor by partial evaporation of the solvent employed in the TEDA quench as a consequence of the supply of heat by the vapor-form TEDA. This significantly reduces or completely prevents desublimation of the vapor-form TEDA and the consequent blockage problems caused by solid deposits in the discharge lines.

The TEDA employed and to be evaporated in the process according to the invention can be obtained by known processes, for example by reaction of monoethanolamine, diethanolamine, triethanolamine, ethylenediamine, diethylenetriamine, triethylenetetraamine, piperazine, N-(2-hydroxyethyl)piperazine, N,N'-bis(2-hydroxyethyl)piperazine, N-(2-aminoethyl)piperazine, N,N'-bis(2-aminoethyl)piperazine, morpholine or mixtures thereof on a catalyst [for example metal pyrophosphates, metal phosphates (such as alkaline-earth metal monohydrogen phosphate), zeolites, zirconium phosphates, $Al_2O_3$, $SiO_2$, phosphorus-containing $TiO_2$ or $ZrO_2$] at elevated temperature (in general from 250 to 450° C.). The pressure here is usually from 0.1 to 50 bar, in particular from 0.1 to 5 bar. The reaction can optionally be carried out in the presence of an inert polar aprotic solvent (for example N-alkylpyrrolidone (such as N-methylpyrrolidone), dioxane, THF, dialkylformamide (such as dimethylformamide), dialkylacetamide (such as dimethylacetamide) and an inert carrier gas (for example $N_2$ or Ar).

Processes of this type are described, for example, in DT-A-24 42 929, U.S. Pat. No. 3,297,701, DE-A-36 34 258, DE-A-1 745 627, DE-A-37 18 395, EP-A-111 928, EP-A-382 055, EP-A-842 935, EP-A-842 936, EP-A-831 096, EP-A-952 152 and U.S. Pat. No. 5,741,906.

According to a preferred embodiment, the process according to the invention can be carried out as follows:

A mixture comprising TEDA obtained, for example, as reaction product in a continuous process by reaction of ethylenediamine and piperazine in a gas-phase reactor at from 320 to 420° C. and from 0.5 to 1.5 bar in the presence of a diluent (for example water), a carrier gas (for example $N_2$ or Ar) and a zeolite catalyst (for example in accordance with the earlier German patent application 10061863.4 of Dec. 12, 2000), is passed into a distillation apparatus having a distillation column with, for example, about 15 theoretical plates. Low-boiling components (such as ammonia, ethylamine and water) are separated off here at the top at a top temperature of from 95 to 120° C. and a pressure of in general from 500 mbar to 1.5 bar. The bottom product is pumped into a further distillation column having, for example, about 30 theoretical plates. At a top temperature of from 140 to 160° C. and a pressure of in general from 500 mbar to 1.5 bar, piperazine is separated off at the top of this column and optionally fed back into the synthesis reactor.

The addition according to the invention of a liquid solvent or diluent (for example NMP) in whose presence the TEDA is later evaporated (see below) takes place in this column. The solvent or diluent is advantageously added to the bottom of the column. The bottom product comprising TEDA and the solvent or diluent is pumped into a further distillation column having, for example, about 25 theoretical plates. At a pressure of in general from 500 mbar to 1.5 bar, the solvent or diluent added to the previous column is separated off from the side take-off in this column and optionally fed back into the previous column or discharged together with the high-boiling components via the bottom product. TEDA is taken off in vapor form at the top of the column in a purity of greater than 95% by weight, in particular greater than 97% by weight, and quenched directly and simultaneously dissolved in a solvent (for example pentane or dipropylene glycol) in a falling-film condenser at a temperature of in general from 30 to 100° C., preferably from 30 to 60° C. (TEDA quench).

EXAMPLES

Example 1

(Comparative Example)

The experiments were carried out in a 4 l (catalyst volume) salt-bath reactor (tube bundle comprising 7 tubes, internal diameter 21 mm, length 2 m) of stainless steel heated by means of electrical heating bands. Some of the pipelines for the reactor feed, reactor product and distillation part were designed as double-walled pipes and oil-heated. The plant parts were protection-heated and were matched individually to the respective temperature necessary for the use of different heating circuits. The catalyst used was a zeolite in the form of pellets (diameter about 2 mm, length about 30 mm) (catalyst bed).

The starting material of 1300 g/h and 3 l (s.t.p.)/h (1 (s.t.p.)=liters at standard temperature and pressure) of nitrogen were passed at atmospheric pressure into the salt-bath reactor heated to 350° C. (space velocity: 1 kg of starting material per 1 of cat. (bed volume) and per h)).

The starting material had the following composition (data in % by weight):

| | | |
|---|---|---|
| | Ethylenediamine (EDA) | 30% |
| | Piperazine (PIP) | 20% |
| | Water | 50% |

The vapor-form reaction product was condensed at 80° C. in a quench with circulating liquid consisting of previously cooled liquid reaction product (see below) (=reaction product quench).

Analysis of the condensate gave the following composition (data in % by weight):

| | |
|---|---|
| Ammonia | 3% |
| Piperazine (PIP) | 17% |
| Triethylenediamine (TEDA) | 23% |
| Water | 54% |
| Remainder | high-boiling components and other by-products |

The uncondensed components were discharged into the distillation column K 200 after a gas/liquid separator.

Some of the liquid reaction product was cooled and used as liquid circuit (for the reaction product quench), and a further part was pumped continuously into a distillation column (K 200) by means of a pump. The glass column having a diameter of 50 mm was fitted with 30 bubble-cap trays. The reflux ratio was about 1:1.

The low-boiling components (ammonia, ethylamine and water) were taken off in liquid form at the top of the column at atmospheric pressure and a top temperature of 96° C.

Analysis of the low-boiling fraction gave the following composition (data in % by weight):

| | | |
|---|---|---|
| | Ammonia | 13% |
| | Ethylamine | 2% |
| | Piperazine (PIP) | 2% |
| | Water | 83% |

The bottom product from the distillation column was pumped continuously into a downstream distillation column K 300 at 155° C. The glass column having a diameter of 50 mm was fitted with 60 bubble-cap trays. The reflux ratio was about 10:1. Piperazine was taken off in liquid form at the top of the column at atmospheric pressure and a top temperature of 150° C. and fed back to the reactor.

Analysis of the distillate fraction gave the following composition (data in % by weight):

| | | |
|---|---|---|
| | Piperazine (PIP) | 93% |
| | Triethylenediamine (TEDA) | 6% |
| | Water | 1% |

The bottom product from the distillation column was pumped continuously into a downstream distillation column K 400 at 184° C. Analysis of the bottom product gave the following composition (data in % by weight):

| | |
|---|---|
| Piperazine (PIP) | 0.2% |
| Triethylenediainine (TEDA) | 83% |
| Remainder | high-boiling components and other by-products |

The glass column K 400 having a diameter of 50 mm was fitted with 50 bubble-cap trays. The reflux ratio was about 8:1. The high-boiling components were removed continuously at 230° C. at the bottom of the column, and the starting temperature of the oil-heated evaporator was 260° C.

TEDA was taken off in vapor form at the top of the column and quenched and simultaneously dissolved at about 30° C. in the liquid solvent pentane (mixture of 80% by weight of n-pentane and 20% by weight of isopentane) (=TEDA quench). A falling-film condenser (trickle-film or falling-stream condenser) in which vapor-form TEDA was introduced from the top was employed for the TEDA quench. The pentane was fed in tangentially at the top of the falling-film condenser.

The resultant solution had the following composition (data in % by weight):

| | | |
|---|---|---|
| | Pentane | 91.8% |
| | Piperazine (PIP) | 0.2% |
| | Triethylenediamine (TEDA) | 8% |

After the pentane had been separated off by evaporation crystallization at 25° C. under nitrogen, TEDA was obtained in a purity of at least 95% by weight.

The TEDA obtained in this way had unsatisfactory properties with respect to its color and odor and was therefore unmarketable.

The TEDA obtained smelled of cyclic saturated N-heterocyclic compounds having a 5-membered ring or other cyclic saturated N-heterocyclic compounds having a 6-membered ring and/or aromatic N-heterocyclic compounds having a 5- or 6-membered ring.

The high temperature necessary in the stripping section of the distillation column K 400 (product temperature up to 230° C.) resulted in considerable thermal load on the TEDA and the high-boiling components and thus in the formation of undesired decomposition products.

By balancing the feed and outflow streams of the column, it can be concluded that there is a piperazine source at the bottom of K 400. The PIP source at the bottom of K 400 is assumed to be the decomposition of high-boiling components (for example aminoethylpiperazine).

Example 2

(According to the Invention)

The experiment was carried out as in Example 1, but with addition of the solvent N-methyl-2-pyrrolidone to K 300.

200 g/h of N-methyl-2-pyrrolidone were fed into the bottom of column K 300.

The bottom product from the distillation column was pumped continuously into the downstream distillation column K 400 at 185° C.

Analysis of the bottom product gave the following composition (data in % by weight):

| | |
|---|---|
| Piperazine (PIP) | 0.03% |
| Triethylenediamine (TEDA) | 53% |
| N-methyl-2-pyrrolidon | 43% |
| Remainder | high-boiling components and other by-products |

The glass column K 400 having a diameter of 50 mm was fitted with 50 bubble-cap trays. The reflux ratio was about 8:1. The solvent N-methyl-2-pyrrolidone and the high-boiling components were removed continuously at the bottom of the column at 200° C., and the starting temperature of the oil-heated evaporator was 230° C. TEDA was taken off in vapor form (gas form) at the top of the column and quenched and simultaneously dissolved at about 30° C. in the solvent pentane (mixture of 80% by weight of n-pentane and 20% by weight of isopentane) (=TEDA quench). A falling-film condenser (trickle-film or falling-stream condenser) in which vapor-form TEDA was introduced from the top was employed for the TEDA quench. The pentane was fed in tangentially at the top of the falling-film condenser. The resultant solution had the following composition (data in % by weight):

| | |
|---|---|
| Pentane | 94.99% |
| Piperazine (PIP) | 0.01% |
| Triethylenediamine (TEDA) | 5% |

After pentane had been separated off by evaporation crystallization at 25° C. under nitrogen, TEDA was obtained in a purity of at least 99.5% by weight.

A 33% strength by weight solution of the resultant TEDA in dipropylene glycol (DPG) had an APHA color number of 26.

The resultant TEDA did not smell of cyclic saturated N-heterocyclic compounds having a 5-membered ring or other cyclic saturated N-heterocyclic compounds having a 6-membered ring and/or aromatic N-heterocyclic compounds having a 5- or 6-membered ring.

Example 3
(According to the Invention)

When the experiment was carried out as described in Example 2, but using dipropylene glycol (DPG) instead of pentane as solvents for the TEDA quench and without subsequent crystallization of the TEDA from the solvent, the following result was obtained.

Composition of the TEDA/DPG solution (data in % by weight):

| | |
|---|---|
| Piperazine (PIP) | 0.05% |
| Triethylenediamine (TEDA) | 33% |
| Dipropylene glycol | 66.95% |

This TEDA/DPG solution had an APHA color number of 55 and can be employed directly as catalyst in the preparation of polyurethanes.

The TEDA/DPG solution obtained did not smell of cyclic saturated N-heterocyclic compounds having a 5-membered ring or other cyclic saturated N-heterocyclic compounds having a 6-membered ring and/or aromatic N-heterocyclic compounds having a 5- or 6-membered ring.

We claim:

1. A process for the preparation of a solution of pure triethylenediamine (TEDA), which comprises evaporating TEDA from a mixture comprising a solvent or diluent, where the solvent or diluent has a boiling point at atmospheric pressure in the range from 175 to 250° C., and introducing the vapor-form TEDA into a liquid solvent.

2. A process as claimed in claim 1, wherein the vapor-form TEDA is obtained at the top or at a side take-off of a distillation or rectification column.

3. A process for the preparation of pure triethylenediamine (TEDA), which comprises preparing a solution of pure TEDA as claimed in claim 1 and subsequently crystallizing the TEDA out of this solution.

4. A process as claimed in claim 1, wherein the solvent or diluent present in the mixture from which the TEDA is evaporated is selected from the group consisting of polar aprotic solvents, non-aromatic cyclic or acyclic hydrocarbons, chlorinated aliphatic hydrocarbons, aromatic hydrocarbons, chlorinated aromatic hydrocarbons, alcohols, amines, N-alkylamides and mixtures thereof.

5. A process as claimed in claim 4, wherein the polar aprotic solvent is selected from the group consisting of N-alkyl-2-pyrrolidones, ethers, ketones, lactones, sulfoxides, carboxylic acid esters, nitrites and ureas.

6. A process as claimed in claim 1, wherein the solvent or diluent present in the mixture from which the TEDA is evaporated has a boiling point at atmospheric pressure in the range from 180 to 230° C.

7. A process as claimed in claim 1, wherein a thin-film evaporator or falling-film evaporator is employed for the evaporation of the TEDA.

8. A process as claimed in claim 1, wherein the liquid solvent into which the vapor-form TEDA is passed is selected from the group consisting of non aromatic cyclic or acyclic hydrocarbons, chlorinated aliphatic hydrocarbons, aromatic hydrocarbons, alcohols, ketones, aliphatic carboxylic acid esters, aliphatic nitriles and ethers.

9. A process as claimed in claim 8, wherein the liquid solvent employed is pentane or dipropylene glycol.

10. A process as claimed in claim 8, wherein the vapor-form TEDA for passing into the liquid solvent has a purity of greater than 95% by weight.

11. A process as claimed in claim 1, wherein the TEDA to be evaporated from a mixture comprising a solvent or diluent has been obtained by reaction of monoethanolamine, diethanolamine, triethanolamine, ethylenediamine, diethylenetriamine, triethylenetetraamine, piperazine, N-(2-hydroxyethyl)piperazine, N,N'-bis(2-hydroxyethyl)piperazine, N-(2-aminoethyl)piperazine, N,N'-bis(2-aminoethyl)piperazine, morpholine or mixtures thereof on a catalyst at elevated temperature.

12. A process as claimed in claim 11, wherein the catalyst is a metal phosphate or a zeolite.

13. A process as claimed in claim 11, wherein the reaction is carried out in the gas phase at a temperature of from 250 to 450° C.

* * * * *

UNITED STATES PATENT AND TRADEMARK OFFICE
CERTIFICATE OF CORRECTION

PATENT NO. : 6,552,194 B2
DATED : April 22, 2003
INVENTOR(S) : Lang et al.

It is certified that error appears in the above-identified patent and that said Letters Patent is hereby corrected as shown below:

<u>Column 10,</u>
Line 41, "nitrites" should be -- nitriles --.

Signed and Sealed this

First Day of July, 2003

JAMES E. ROGAN
*Director of the United States Patent and Trademark Office*